US 7,935,079 B2

(12) United States Patent
Ludin et al.

(10) Patent No.: US 7,935,079 B2
(45) Date of Patent: *May 3, 2011

(54) TROUBLESHOOTING ACCELERATOR SYSTEM FOR IMPLANTABLE DRUG DELIVERY PUMPS

(75) Inventors: Lev Ludin, Newton, MA (US); Brooke W. Mastrorio, Lakeville, MA (US); Timothy Beardsley, Kingston, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1344 days.

This patent is subject to a terminal disclaimer.

(21) Appl. No.: 11/427,061

(22) Filed: Jun. 28, 2006

(65) Prior Publication Data

US 2006/0253105 A1   Nov. 9, 2006

Related U.S. Application Data (63) Continuation of application No. 11/141,066, filed on May 31, 2005, now Pat. No. 7,089,783, which is a continuation of application No. 10/348,812, filed on Jan. 22, 2003, now Pat. No. 6,902,544.

(51) Int. Cl.
*A61M 31/00* (2006.01)
(52) U.S. Cl. ................................. 604/93.01; 604/131
(58) Field of Classification Search .................. 604/131, 604/890.1, 891.1, 502, 93.01, 141, 132, 133, 604/145, 175
See application file for complete search history.

(56) References Cited

U.S. PATENT DOCUMENTS

| | | | |
|---|---|---|---|
| 4,003,379 A | 1/1977 | Ellinwood, Jr. | |
| 4,373,527 A | 2/1983 | Fischell | |
| 4,398,908 A | 8/1983 | Siposs | |
| 4,443,218 A | 4/1984 | De Cant | |
| 4,784,645 A | 11/1988 | Fischell | |
| 5,000,664 A | 3/1991 | Lawless et al. | |
| 5,207,642 A | 5/1993 | Orkin et al. | |
| 5,474,552 A | 12/1995 | Palti | |
| 5,476,005 A | 12/1995 | Lindegren et al. | |
| 5,575,770 A | 11/1996 | Melsky et al. | |
| 5,584,671 A | 12/1996 | Schweitzer et al. | |
| 5,711,316 A | 1/1998 | Eisberry et al. | |
| 5,769,823 A | 6/1998 | Otto | |
| 5,782,798 A | 7/1998 | Rise | |

(Continued)

FOREIGN PATENT DOCUMENTS

GB            1549315          2/1976

(Continued)

*Primary Examiner* — Nicholas D Lucchesi
*Assistant Examiner* — Laura A Bouchelle
(74) *Attorney, Agent, or Firm* — Nutter McClennen & Fish LLP (57) ABSTRACT

An implantable pump and methods for detecting leaks in an implantable pump are provided. In one embodiment, the implantable drug pump includes a housing having at least one inlet port and an outlet port formed therein. The outlet port is adapted to communicate with a catheter for delivering fluid to a patient's body, and the inlet port(s) are effective to deliver fluid into the housing. The housing further includes at least one reservoir disposed therein and effective to contain a fluid. In use, the pump preferably includes a fluid having one or more drugs disposed in at least one of the reservoirs, and a radiopaque fluid disposed in one of the reservoirs. A user programmable control mechanism is coupled to the drug pump and is effective to selectively control movement of the valves between the open and closed positions.

15 Claims, 8 Drawing Sheets

U.S. PATENT DOCUMENTS

| | | |
|---|---|---|
| 5,797,898 A | 8/1998 | Santini, Jr. et al. |
| 5,978,702 A | 11/1999 | Ward et al. |
| 6,010,492 A | 1/2000 | Jacobsen et al. |
| 6,016,449 A | 1/2000 | Fischell et al. |
| 6,056,734 A | 5/2000 | Jacobsen et al. |
| 6,554,822 B1 * | 4/2003 | Holschneider et al. .... 604/892.1 |
| 6,731,216 B2 | 5/2004 | Ho et al. |
| 6,902,544 B2 * | 6/2005 | Ludin et al. ............. 604/93.01 |
| 7,563,255 B2 * | 7/2009 | Adamis et al. ............ 604/294 |
| 2003/0009131 A1 | 1/2003 | Van Antwerp et al. |
| 2003/0225380 A1 | 12/2003 | Redl et al. |

FOREIGN PATENT DOCUMENTS

| | | |
|---|---|---|
| WO | WO-94 04095 | 3/1994 |
| WO | WO 9404095 A1 * | 3/1994 |
| WO | WO-03 004034 | 1/2003 |

* cited by examiner

TROUBLESHOOTING ACCELERATOR SYSTEM FOR IMPLANTABLE DRUG DELIVERY PUMPS

CROSS-REFERENCE TO RELATED APPLICATIONS

This application is a continuation of U.S. patent application Ser. No. 11/141,066 filed on May 31, 2005 and entitled "Troubleshooting Accelerator System for Implantable Drug Delivery Pumps," which is a continuation of U.S. patent application Ser. No. 10/348,812 (now U.S. Pat. No. 6,902,544) filed on Jan. 22, 2003 and entitled "Troubleshooting Accelerator System for Implantable Drug Delivery Pumps," which are hereby incorporated by reference in their entireties.

FIELD OF THE INVENTION

The present invention relates to implantable drug pumps and methods for detecting leaks in an implantable drug pump.

BACKGROUND OF THE INVENTION

Implantable drug delivery devices are commonly used to provide site specific and/or sustained delivery of beneficial agents to address adverse patient conditions. The pumps are used for the continuous medication delivery over relatively long periods of time in patients who could otherwise only be treated by injecting the medications, such as, e.g., morphines, heparins and similar drugs, several times daily. Pumps are advantageous in comparison with injections in that an even flow rate and a significantly lower total intake of the drug can be realized.

Implantable drug pumps typically include a reservoir for storing a fluid, such as a drug, and a pump or other flow control device to deliver the fluid to a site within a patient. A septum is formed on the top of the pump to allow refilling of the reservoir. Most implantable pumps also include a bolus port which is coupled to the catheter to enable a one-time injection directly to the treatment site. In use, the pump is disposed in a subcutaneous pocket in the area of the abdomen of the patient whereby the refill opening sealed by the septum is palpable under the skin of the patient. The medication reservoir is filled by piercing the skin of the patient and the septum with the corresponding needle of a syringe.

While implantable pumps have been proven to be highly effective, one disadvantage of current designs is the inability to detect leaks in the catheter extending from the pump to the drug delivery site, or between the catheter and the outlet port. Currently, leak detection requires the drug to be removed from the drug reservoir, and sodium chloride to be introduced through the refill port. The pump is then set to dispense the sodium chloride until any residual drug is removed from the reservoir. This process alone can take several days to complete. Once the reservoir is emptied, a contrast agent can then be introduced through the bolus port. An x-ray image of the contrast agent flowing through the catheter is then taken to detect any leaks.

Accordingly, there is a need for improved drug pumps, and for methods for detecting leaks in a drug pump.

SUMMARY OF THE INVENTION

In general, the present invention provides implantable drug pumps and methods for detecting leaks in an implantable drug pump. In one embodiment, an implantable drug pump is provided having a housing including an inlet port and an outlet port formed therein. The outlet port is adapted to communicate with a catheter for delivering fluid to a patient's body, and the inlet port is effective to deliver fluid into the housing. The housing further includes at least one reservoir disposed therein that is effective to contain a fluid. In use, the pump preferably includes a fluid having one or more drugs disposed in at least one of the reservoirs, and a radiopaque fluid disposed in another one of the reservoirs. A user programmable control mechanism is coupled to the drug pump and is effective to selectively control movement of the valves between the open and closed positions.

In one embodiment, the reservoirs can be selectively rotatable within the housing such that any one of the reservoirs can be positioned to be in fluid communication with the outlet port, and any one of the reservoirs can be positioned to be in fluid communication with the inlet port. The pump further includes at least one valve disposed between the reservoirs and the outlet port. The valve is effective to control the flow of fluid from the reservoirs to the outlet port. A driver mechanism is provided and is effective to selectively drive fluid from the reservoirs to the outlet port.

In another embodiment the drug pump can include several valves, each valve being in communication with one of the reservoirs and in fluid communication with the outlet port. A controller is preferably in communication with each of the valves for selectively moving each of the valves between an open position and a closed position. An external programmer is preferably provided for actuating the controller. In an exemplary embodiment, each valve includes a latch member mated to a plunger movable between an open and closed position, and an actuator mechanism effective to actuate the latch member and move the plunger between the open and closed positions. The actuator mechanism is preferably a piezoelectric actuator, however a variety of actuator mechanisms can be used.

In yet another embodiment of the present invention, an implantable drug pump is provided having a housing including an inlet port and a plurality of outlet ports formed therein. The plurality of outlet ports are adapted to communicate with at least one catheter for delivering fluid to a patient's body, and the inlet port is effective to deliver fluid into the housing. The pump further includes a plurality of reservoirs disposed within the housing and effective to contain a fluid therein. Each of the plurality of reservoirs is in fluid communication with at least one of the plurality of outlet ports and with the inlet port. The pump also includes a plurality of valves, each valve being disposed between one of the plurality of reservoirs and one of the plurality of outlet ports. The plurality of valves are effective to control the flow of fluid from the plurality of reservoirs to the plurality of outlet ports. The pump can also include a driver mechanism effective to selectively drive fluid from the plurality of reservoirs to the plurality of outlet ports.

A method for detecting a leak in an implantable drug pump is also provided. The method includes the step of providing an implantable drug pump having a housing including a first reservoir disposed therein and containing a fluid having one or more drugs, and a second reservoir disposed therein and containing a radiopaque fluid. The housing further includes at least one inlet port formed therein that is in communication with at least one of the first and second reservoirs, an outlet port formed therein and adapted to deliver a fluid to a patient's body. A first programmable valve is in fluid communication with the first reservoir and the outlet port. The first valve is movable between a closed position, in which fluid is prevented from flowing from the first reservoir to the outlet port, and an open position, in which fluid is free to flow from the first reservoir to the outlet port. A second programmable valve is in fluid communication with the second reservoir and the outlet port. The second valve is movable between a closed position, in which fluid is prevented from flowing from the second reservoir to the outlet port, and an open position, in which fluid is free to flow from the second reservoir to the outlet port. The pump also includes a driver mechanism effective to drive fluid from the first and second reservoirs to the outlet port for delivering fluid to a patient's body. The method further includes the steps of causing the first valve to move to the closed position, causing the second valve to move to the open position, and actuating the driver mechanism to cause the radiopaque fluid disposed within the second reservoir to flow through the valve and into the outlet port to be delivered to a patient's body. The flow of radiopaque fluid through the pump can be radiographically viewed to determine if any leaks exist in the implantable drug pump. Prior to the steps of programming the first and second valves and actuating the driver mechanism, the radiopaque fluid can optionally be introduced into the second reservoir through the second inlet port.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides implantable drug pumps and methods for detecting leaks in an implantable drug pump. In general, the implantable drug pump includes a housing having an inlet port and at least one outlet port formed therein. The outlet port is adapted to communicate with a catheter for delivering fluid to a patient's body, and the inlet port is effective to deliver fluid into two or more reservoirs disposed within the housing and effective to contain the fluid. The reservoirs can be fixedly disposed within the housing, or alternatively the reservoirs can be selectively rotatable within the housing such that any one of the reservoirs can be positioned to be in fluid communication with at least one outlet port, and any one of the reservoirs can be positioned to be in fluid communication with the inlet port. The pump can also include at least one valve disposed between the reservoirs and the outlet port. The valve is effective to control the flow of fluid from at least one of the reservoirs to the outlet port. A driver mechanism is also provided and is effective to selectively drive fluid from the reservoirs to the outlet port. Preferably, the driver mechanism selectively applies a force to at least one of the reservoirs to cause fluid disposed therein to be forced through the valve, when open, and out the outlet port.

Figure 1:
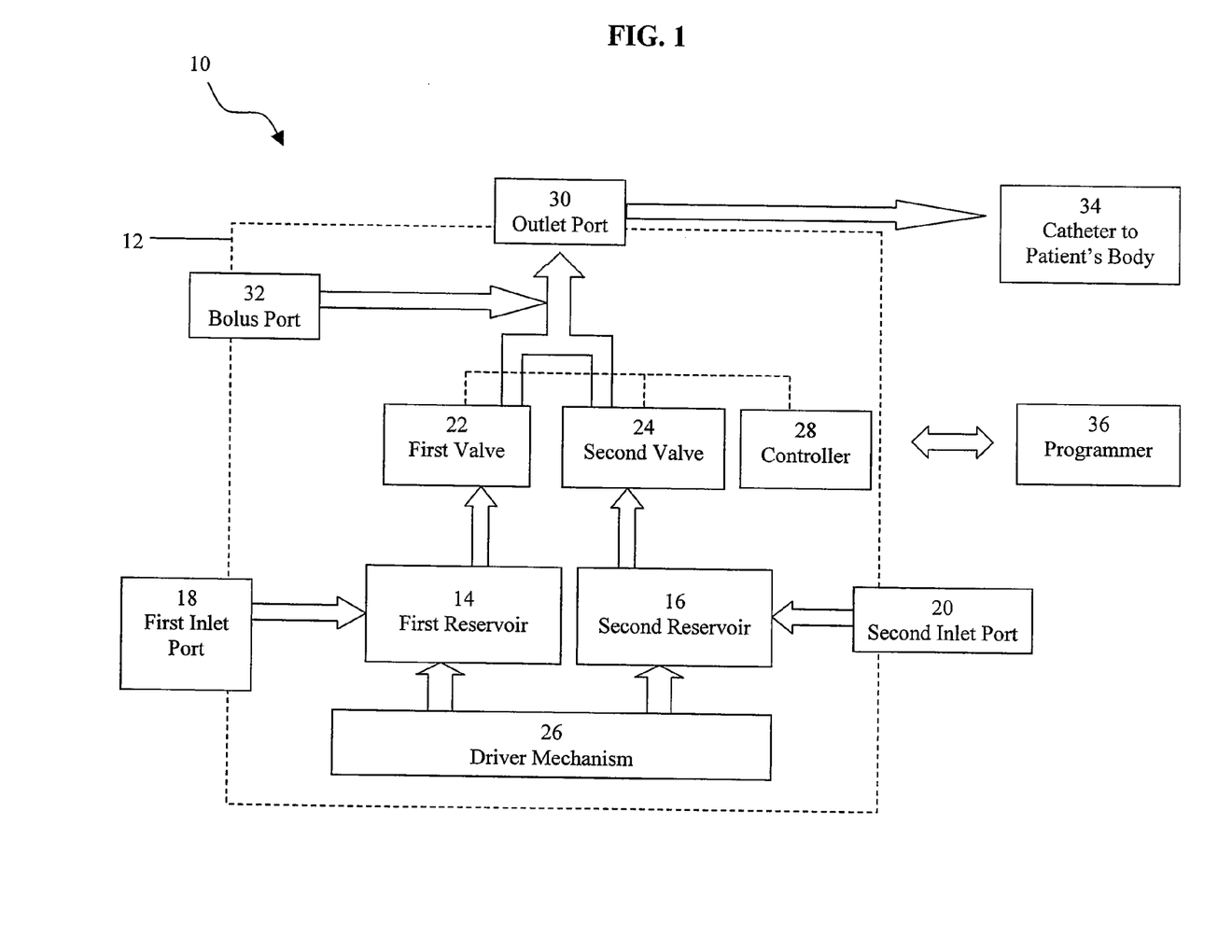
FIG. 1 is schematic diagram illustrating one embodiment of an implantable pump having two reservoirs according to the present invention.

FIG. 1 illustrates a schematic diagram of one embodiment of an implantable drug pump 10 according to the present invention. The pump 10, and the pump components, can each have a variety of shapes, sizes, and configurations. The pump 10 should, however, be adapted to be implanted within a patient's body. As shown in FIG. 1, the pump 10 includes a housing 12 having first and second reservoirs 14, 16 disposed therein and adapted to contain an amount of fluid. The reservoirs 14, 16 are each preferably formed from a bellows that is compressible upon application of a force thereto. Each reservoir 14, 16 is coupled to an outlet port 30 formed in the housing 12 and to first and second inlet ports 18, 20, respectively. Fluid can be introduced into the first reservoir 14 through the first inlet port 18 and the second reservoir 16 through the second inlet port 20, and fluid can exit each reservoir 14, 16 through the outlet port 30. The pump 10 can also optionally include a bolus port 32 coupled directly to the outlet port 30 for enabling the direct delivery of fluid to a patient via catheter 34.

The pump 10 further includes first and second valves 22, 24 disposed between the outlet port 30 and the first and second reservoirs 14, 16, respectively. The valves 22, 24 are effective to control the flow of fluid from the reservoirs 14, 16 to the outlet port 30, and each valve 22, 24 is coupled to a controller 28 disposed within the housing 12. The controller 28 is effective to selectively move each valve 22, 24 between an open position and a closed position. An external programmer 36 can be provided for transmitting a signal to the controller 28 to actuate the valves 22, 24. An exemplary embodiment of a valve for use with a pump according to the present invention will be described in more detail with respect to FIG. 5.

The housing 12 further includes a driver mechanism 26 adapted to drive fluid from the first and second reservoirs 14, 16 through the first and second valves 22, 24, when in the open positions, and out the outlet port 30 whereby the fluid can be delivered to a treatment site within a patient via a catheter 34. A variety of driver mechanisms 26 can be used with the present invention, including both constant-pressure driver mechanisms and programmable driver mechanisms that can apply pressure at variable, programmed rates. The driver mechanism 26 can also be adapted to selectively apply pressure to only one reservoir at a time, or alternatively, the pump 10 can include a separate driver mechanism coupled to each reservoir. The driver mechanism 26 can also optionally be adapted to apply a pulsatile pressure to each reservoir. Suitable driver mechanisms 26 include, for example, a compression spring, a propellant gas, and an electromechanical actuator.

In use, the pump 10 is implanted within a patient, and the first and second reservoirs are filled with fluid, via the inlet ports 18, 20, either prior to or after implantation of the pump 10. The pump programmer 36 is then used to send a signal to the controller to move the valves 22, 24 between the open and closed positions, and optionally to activate the driver mechanism 26, depending on the type of driver mechanism 26 used. As the driver mechanism 26 applies a force to one or both of the reservoirs 14, 16, if the valves 22, 24 are open, fluid is forced out of one or both of the reservoirs 14, 16 and travels through the outlet port 30 to be delivered to a drug delivering site within the patient via catheter 34.

Figure 2:
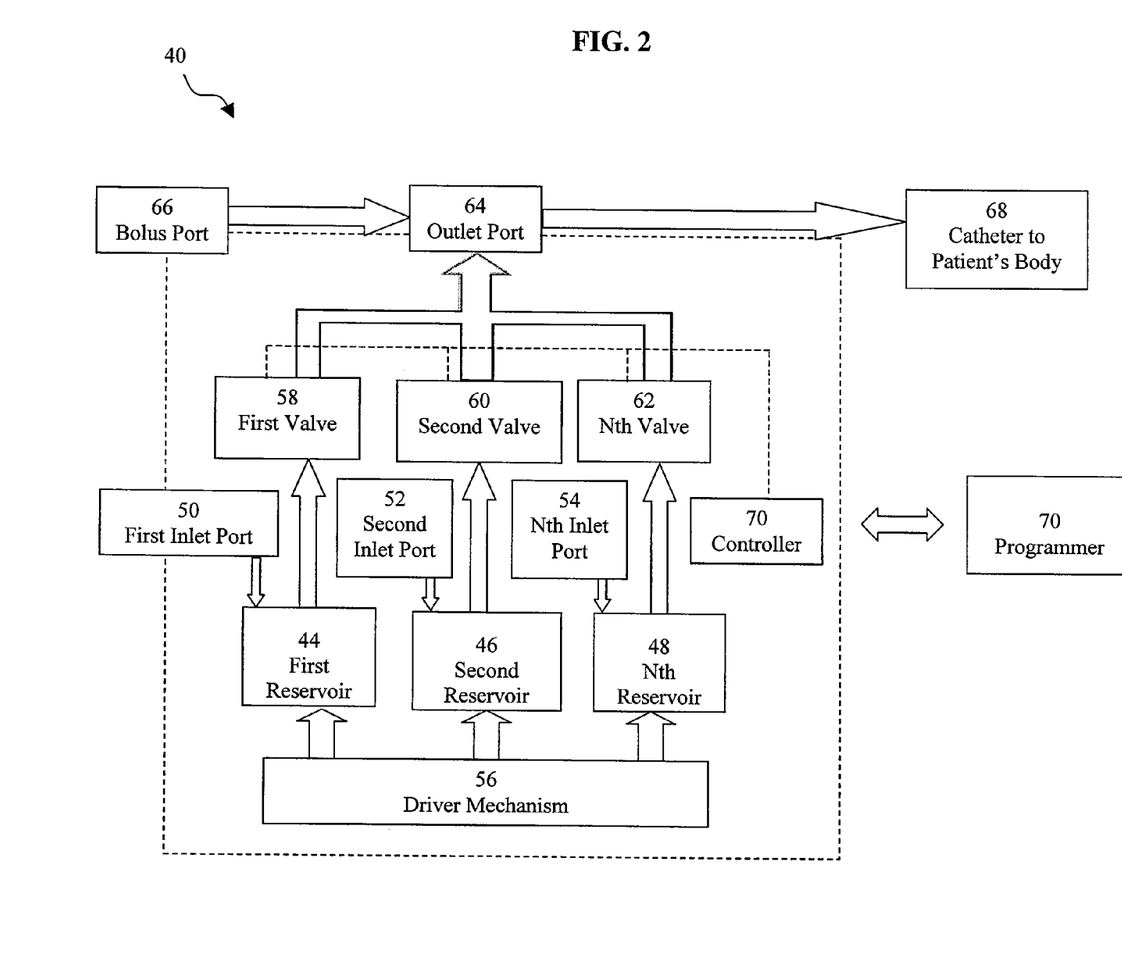
FIG. 2 is a schematic diagram illustrating another embodiment of an implantable pump having multiple reservoirs according to the present invention.

FIG. 2 illustrates another embodiment of an implantable drug pump 40. The pump 40 is similar to the pump 10 shown in FIG. 1, except that the pump 40 includes multiple reservoirs 44, 46, 48. Each reservoir 44, 46, 48 includes an inlet port 50, 52, 54 for introducing fluid into the reservoir 44, 46, 48, and a valve 58, 60, 62 for controlling the flow of fluid from the reservoir 44, 46, 48 to an outlet port 64. While only one outlet port 64 is illustrated, each reservoir 44, 46, 48 can optionally be individually coupled to an outlet port that is in communication with a catheter. This allows fluid to be delivered to difference treatment sites within a patient's body.

The pump 40 operates similar to pump 10 shown in FIG. 1, wherein a driver mechanism 56 is provided for applying a pressure to one or more of the reservoirs 44, 46, 48 to force fluid out of the reservoir 44, 46, 48 when the valve 58, 60, 62 is in the open position. The pump 40 is particularly advantageous in that various combinations of drugs can be administered to a patient individually or simultaneously. Moreover, one of the reservoirs 44, 46, 48 can be reserved for retaining a radiopaque fluid used for testing the pump 14 for leaks.

Figure 3A:
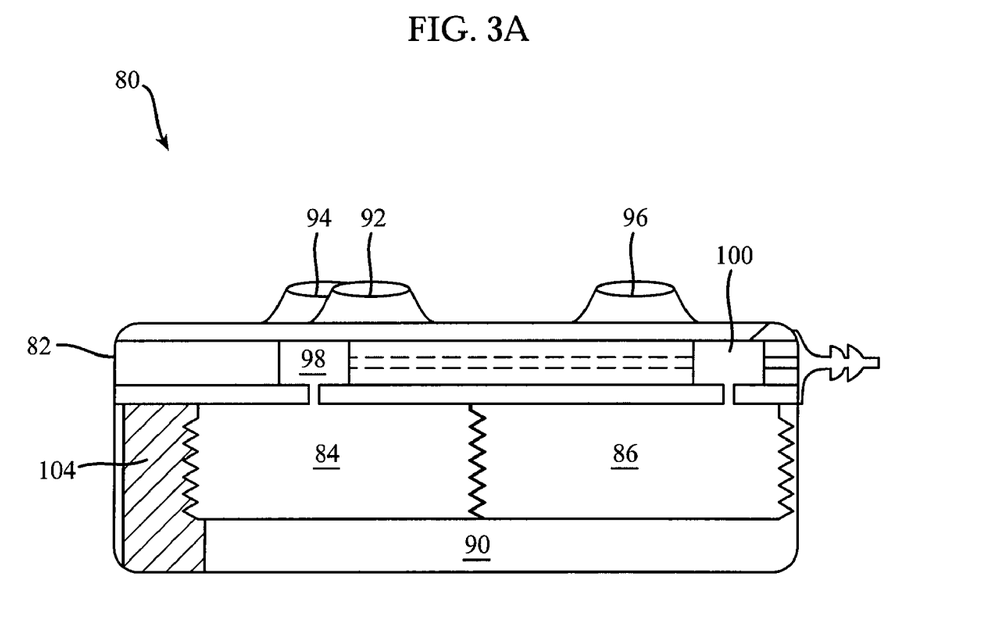
FIG. 3A is a side, sectional view illustration of an implantable pump configured in accordance with the diagram shown in FIG. 2.
Figure 3B:
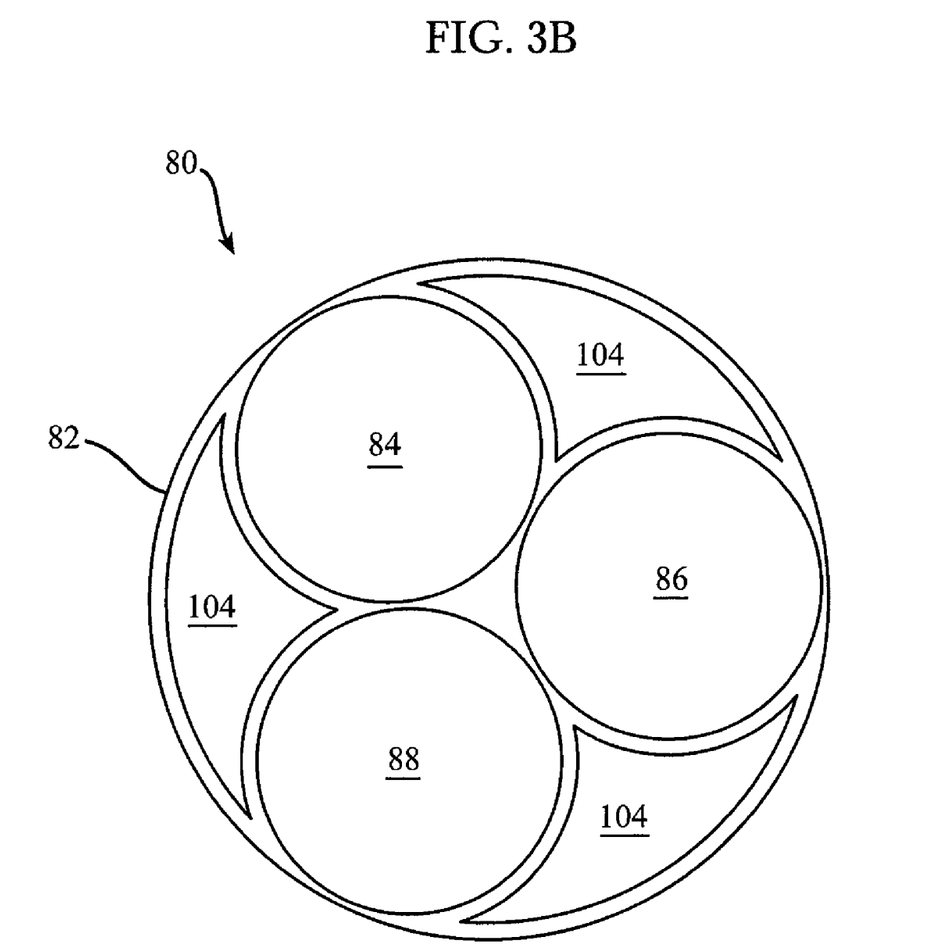
FIG. 3B is a top view of the pump shown in FIG. 3A.

FIGS. 3A and 3B illustrate an exemplary embodiment of a pump 80 constructed in accordance with the schematic diagram shown in FIG. 2. As shown, the pump 80 includes a housing 82 having first, second, and third reservoirs 84, 86, 88 disposed therein. The housing 82 can have a variety of shapes and sizes, but is preferably cylindrical and has a size adapted to contain the pump components. Each reservoir 84, 86, 88 can also vary in shape and size, but preferably each reservoir 84, 86, 88 has a cylindrical shape and is formed from a bellows. The pump 80 further includes first, second, and third inlet ports 92, 94, 96 in fluid communication with the first, second, and third reservoirs 84, 86, 88, respectively, and an outlet port 102 fluidly coupled to all three reservoirs 84, 86, 88. A valve 98, 100 (third valve is not shown) is disposed between each reservoir 84, 86, 88 and the outlet port 102 to control fluid flow from the reservoirs 84, 86, 88 to the outlet port 102.

The pump 80 can also include a variety of additional features including, for example, a controller 104 disposed within the housing 82. The controller 104 is preferably disposed in the chambers 104 between the reservoirs 84, 86, 88 for effecting movement of each valve 98, 100 between an open position and a closed position. As previously described with respect to FIGS. 1 and 2, an external programmer can be used to transmit a signal to the controller 104 to effect movement of each valve 98, 100 between the open and closed positions. The pump 80 also preferably includes a driver mechanism 90 that is effective to apply pressure to one or more of the reservoirs 84, 86, 88 to drive fluid out of the reservoirs 84, 86, 88. As previously described above, a variety of driver mechanisms can be used with a pump according to the present invention, including, for example, a propellant gas.

A person having ordinary skill in the art will appreciate that the configuration of the driver mechanism 90 can vary, and that one or more driver mechanisms 90 can be provided to enable each reservoir 84, 86, 88 to be actuated either simultaneously or independently of one another. By way of non-limiting example, a single driver mechanism can be provided to apply pressure to all three reservoirs simultaneously, or alternatively, each reservoir can be coupled to a separate driver mechanism thereby allowing each reservoir to be actuated independently. In yet another embodiment, the driver mechanism 90 can be movably disposed within the housing to allow the driver mechanism to be positioned adjacent any one or more of the reservoirs to drive fluid therefrom.

A person having ordinary skill in the art will appreciate that the pump can include a variety of other features not shown or described herein. By way of non-limiting example, the pump can include a bolus port in fluid communication with the outlet port. In use, fluid can be injected into the bolus port, whereby it flows directly out of the outlet port and is delivered to the patient. The pump also preferably includes a flow-restrictor mechanism disposed between each reservoir and the valve. The flow-restrictor mechanism is effective to control the rate of fluid flow from the reservoir to the valve.

Figure 4A:
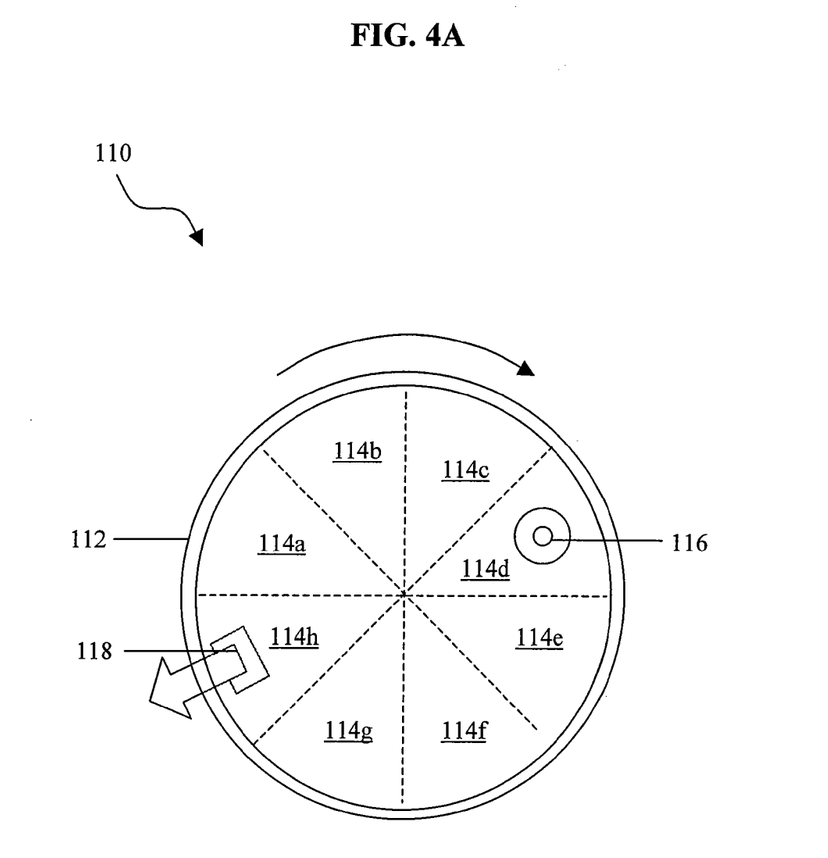
FIG. 4A is a top view illustration of an implantable pump according to another embodiment of the present invention.
Figure 4B:
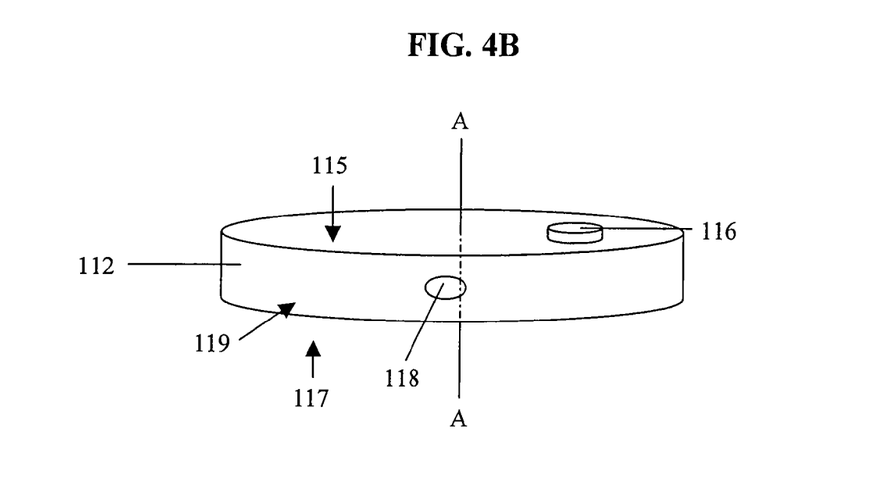
FIG. 4B is a side view illustration of the implantable pump shown in FIG. 4A.

FIGS. 4A and 4B illustrate another embodiment of an implantable pump 110 that includes a housing 112 having several reservoirs 114$a$-$h$ rotationally disposed therein. The housing 112 can have any shape and size, but is preferably cylindrical and includes a proximal end 115, a distal end 117, and a sidewall 119 extending therebetween and forming an inner chamber adapted to contain the reservoirs 114$a$-$h$ and other pump components. The pump 110 further includes an inlet port 116 adapted to communicate with one of the reservoirs 114$a$-$h$, and an outlet port 118 preferably adapted to communicate with another one of the reservoirs 114$a$-$h$. The inlet and outlet ports 116, 118 can be positioned anywhere in the housing 112, but preferably the inlet port 116 is formed in the proximal end 115 of the housing 112, and the outlet port 118 is formed in the sidewall 119 of the housing 112 and positioned apart from the inlet port 116.

Each of the reservoirs 114$a$-$h$ can have virtually any shape or size, but the reservoirs 114$a$-$h$ should be adapted to rotate simultaneously around an axis to enable at least one of the reservoirs 114$a$-$h$ to be fluidly coupled to the inlet port 116, and at least one of the reservoirs 114$a$-$h$ to be fluidly coupled to the outlet port 118. Preferably, the reservoirs 114$a$-$h$ rotate simultaneously around a central axis A-A (FIG. 4B) extending through the pump 110 from the proximal end 115 to the distal end 117. As shown in FIG. 4A, rotation of the reservoirs 114$a$-$h$ enables one of the reservoirs 114$a$-$h$, e.g., reservoir 114$d$, to be coupled to the inlet port 116, and one of the reservoirs 114$a$-$h$, e.g., 114$h$, to be coupled to the outlet port 118. A variety of techniques can be used to effect movement of the reservoirs within the housing, including both mechanical and electrical actuators. Preferably, movement of the reservoirs is controlled by the programmer via a controller (not shown) disposed within the pump.

The pump can also include a variety of other features similar to those previously described with respect to FIGS. 1-3B. By way of non-limiting example, the pump 220 preferably includes a valve (not shown) coupled to the outlet port 118 for controlling the flow of fluid from the reservoir, e.g., reservoir 114$h$, to the outlet port 118 and the catheter (not shown). An exemplary embodiment of a valve will be described in more detail with reference to FIGS. 5A-5C. The pump 110 further includes a driver mechanism (not shown) that is preferably positioned adjacent the outlet port 118, and that is effective to apply a force to the reservoir, e.g. reservoir 114$h$, coupled to the outlet port 118. A variety of driver mechanisms can be used, including those driver mechanisms described above with respect to FIGS. 1-3B.

The present invention also provides a method of using a pump. While the method can be employed using virtually any pump, including those described herein, the method is described in connection with FIG. 1 for illustration purposes only. Referring to FIG. 1, the pump 10 preferably contains a marking agent to enable the pump and/or the catheter 34 to be tested for leaks. Preferably, one of the reservoirs, e.g., the first reservoir 14, contains a drug disposed therein, and the other reservoir, e.g., the second reservoir 16, includes a radiopaque fluid disposed therein. The radiopaque fluid can be a marking agent, or a mixture of a marking agent and a physiologically acceptable sodium chloride solution. The marking agent and/ or sodium chloride solution can be predisposed within the reservoir 16 prior to implantation of the pump 10, or it can be injected into the reservoir 16 via inlet port 20. Preferably, sodium chloride solution is disposed within the reservoir 16, and the marking agent is injected into the reservoir 16 prior to testing the pump 10 for leaks. Once the marking agent is disposed within the second reservoir 16, the programmer 36 can be used to transmit a signal to the controller 28 to move the first valve 22 to the closed position, thereby preventing any fluid from exiting the first reservoir 14, and to move the second valve 24 to the open position, thereby allowing fluid to flow from the second reservoir 16 through the outlet port 30 and to the treatment site via catheter 34. The programmer 36 can also optionally be used to send a signal to the driver mechanism 26 where a variable driver mechanism 26 is employed. While the fluid is flowing through the pump 10 and the catheter 34, a radiographic image, e.g., an x-ray image, of the pump 10 and catheter 34 can be taken and viewed to determine if any leaks exist in the implantable drug pump 10 and/or catheter 34. This is particularly advantageous in that the first reservoir 14 containing the drug does not need to be drained and cleaned to allow the pump 10 to be tested for leaks.

A person having ordinary skill in the art will appreciate that the pumps described herein are not limited to use with a marking agent, and that a variety of drugs can be disposed within the pump and used to treat a patient.

Figure 5A:
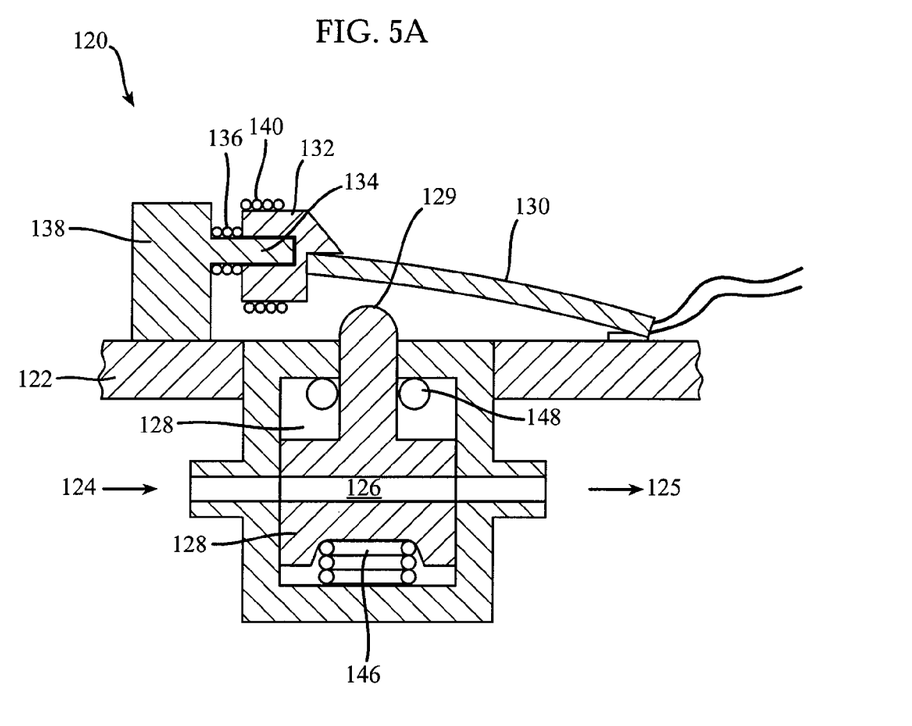
FIG. 5A is a side view illustration of a valve in an open position in accordance with one embodiment of the present invention.
Figure 5B:
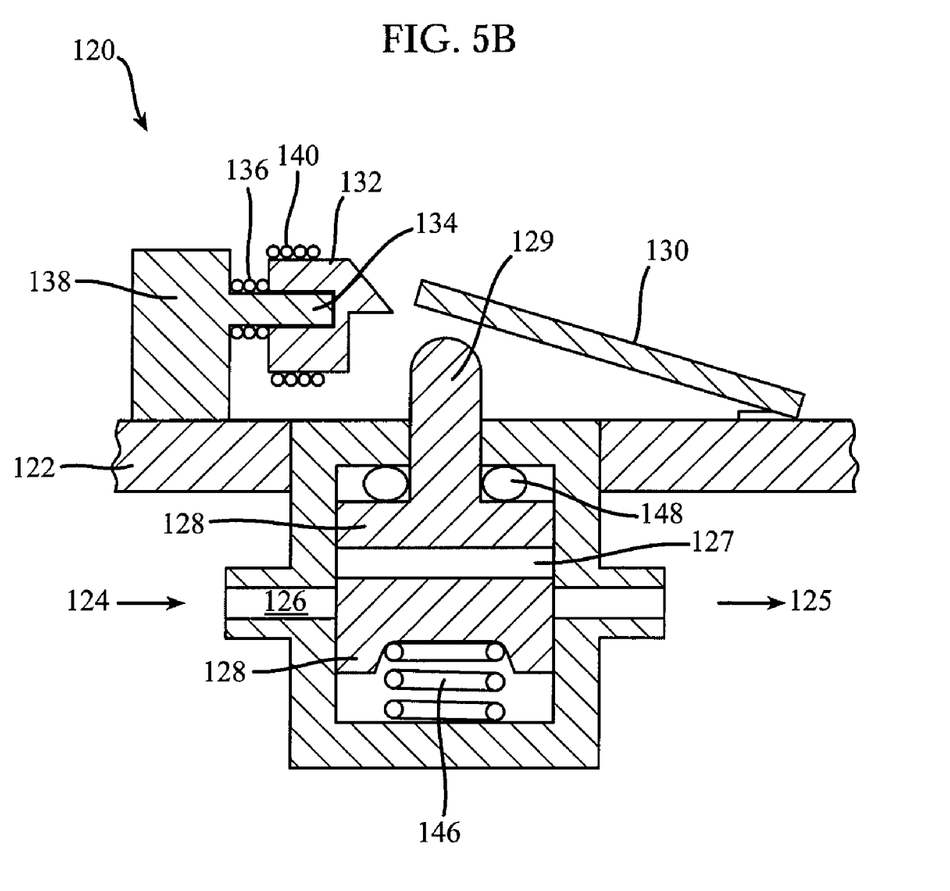
FIG. 5B is a side view illustration of the valve shown in FIG. 5A in a transitional state moving from the open position to a closed position.
Figure 5C:
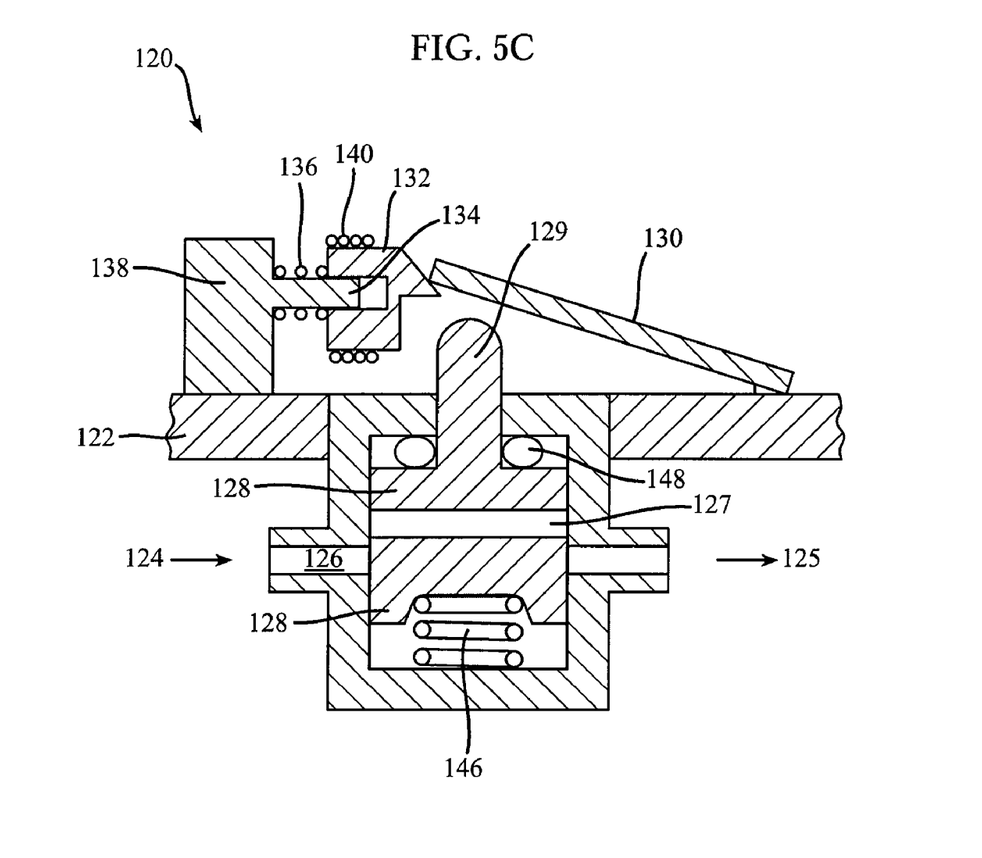
FIG. 5C is a side view illustration of the valve shown in FIG. 5B is a closed position.

FIGS. 5A-5C illustrate an exemplary embodiment of a valve 120 for use with an implantable pump. As shown, the valve 120 includes a housing 122 having an inlet 124, an outlet 125, and an inner lumen 126 extending therebetween. A movable flow control member, e.g., a plunger, is disposed adjacent the inner lumen 126 and includes a proximal portion 129 and a distal portion 128 having an inner lumen 127 (shown in FIG. 5B) extending therethrough. The flow control member 128, 129 is movable between an open position, as shown in FIG. 5A, in which inner lumen 127 is aligned with the inner lumen 126 of the housing 122, and a closed position, shown in FIGS. 5B and 5C, in which the distal portion 128 of the flow control member is moved proximally so that inner lumen 127 is offset from inner lumen 126, thereby blocking inner lumen 126 to prevent fluid from flowing through the housing 122.

The flow control member 128, 129 is coupled to a piezoelectric system which includes several springs 146, 136, 140, a latch 132, and a piezoelectric actuator 130. The piezoelectric system is effective to move the flow control member 128, 129 between the open and closed positions. While a variety of actuation devices can be used, the piezoelectric system includes a latch 132 having a portion positioned around a receiving pin 134 that is coupled to a base structure 138, and an opposed portion that is coupled to the piezo actuator 130. A solenoid 140 is mated to and/or disposed around the latch 132, and a spring member 136 is disposed around the receiving pin 134, and is adapted to be compressed by the latch 132. The spring member 136 is preferably made from a ferromagnetic material such that DC voltage applied to the solenoid 140 will generate a force that is effective to cause the latch 132 to move toward the base structure 138, thereby compressing the spring 136. The piezoelectric actuator 130, which is positioned on the opposed side of the latch 132 from the spring 136, can have a variety of shapes, but preferably has a generally elongate shape and, upon application of a voltage applied thereto, moves between a first and second position, which will be described in more detail herein. The piezoelectric system can also include a receiving member 146 positioned on a side of the inner lumen 126 opposed to the flow control member 128, 129. The receiving member 146 can be, for example, a spring mechanism effective to receive a pressure applied thereto by the flow control member 128, 129. The valve 120 can also include other features such as an o-ring 148 disposed around a portion of the flow control member 128, 129 for enabling movement of the flow control member 128, 129 between the open and closed positions.

In use, the flow control member 128, 129 can be moved between the open and closed positioned by applying DC Voltage to the piezoelectric actuator and the solenoid, respectively. Referring to FIG. 5A, in which no voltage is being applied, the flow control member 128, 129 is shown in the open position, whereby fluid is allowed to pass through the inner lumen 126 in the housing 122 and through the inner lumen 127 in the flow control member 128, 129. Spring 136 is in the uncompressed positioned, while spring 146 is compressed by a downward force from the flow control member 128, 129. The piezoelectric actuator 130 is being engaged by the latch 132 to hold the flow control member 128, 129 in a distal position, thereby applied a downward pressure to compress spring 146, and to allow fluid to flow through lumens 126 and 127.

FIG. 5B illustrates a transitional state as the flow control member moves from the open position to the closed position. Movement of the flow control member can be activated by applying a DC Voltage to the solenoid 140, which generates a force to move the latch 132 toward the base structure 138, thereby compressing spring 136 and releasing the piezoelectric actuator 130 from the engaged position. The flow control member 128, 129 can then move in a proximal direction to the closed position, thereby blocking the flow of fluid through the lumen 126 formed in the housing 122. Once the voltage source is shut off, the latch 132 is then released and spring 136 is free to return to the uncompressed state, as shown in FIG. 5C. Movement of the latch 132 back to the original state engages and pushes the piezoelectric actuator 130 upward in a proximal direction.

In order to return the flow control member 128, 129 to the open position, DC Voltage can be applied to the piezoelectric actuator 130, thereby causing the actuator 130 to apply a distal force on the latch 132 to push the latch 132 toward the base structure 138, thereby compressing spring 136. Once the actuator 130 moves distally past the latch 130, the latch 132 is then released and spring 136 is free to return to the uncompressed state. The latch 32 then engages the piezoelectric actuator 130 to hold the flow control member 128, 129 in a distal, open position, as shown in FIG. 5A.

A person having ordinary skill in the art will appreciate that a variety of valves can be used with a pump according to the present invention, and that the valve can include a variety of actuation mechanisms. By way of non-limiting example, both mechanical and electrical devices can be used to actuate the valve, include, for example, a shape memory material.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. An implantable drug pump, comprising:
a plurality of reservoirs selectively rotatably disposed within a housing such that any one of the plurality of reservoirs can be positioned to be in fluid communication with an outlet port formed in the housing, and any one of the plurality of reservoirs can be positioned to be in fluid communication with an inlet port formed in the housing;

at least one valve disposed between the plurality of reservoirs and the outlet port, the at least one valve being movable from a closed position to an open position and back to a closed position to control the flow of fluid from the plurality of reservoirs to the outlet port; and a driver mechanism effective to selectively drive fluid from the plurality of reservoirs to the outlet port.

2. The implantable drug pump of claim 1, wherein the driver mechanism is selected from the group consisting of a spring, a propellant gas, and an electromechanical actuator.

3. The implantable drug pump of claim 1, wherein the driver mechanism is adapted to selectively apply a force to at least one of the plurality of reservoirs to cause fluid disposed within the reservoir to be forced through the at least one valve and the outlet port.

4. The implantable drug pump of claim 1, wherein the at least one valve comprises a plurality of valves, each valve being in fluid communication with the outlet port and one of the plurality of reservoirs.

5. The implantable drug pump of claim 4, further comprising a controller in communication with the plurality of valves for selectively moving each of the plurality of valves between an open position and a closed position, and an external programmer effective to actuate the controller.

6. An implantable drug pump, comprising:
a plurality of reservoirs selectively rotatably disposed within a housing such that any one of the plurality of reservoirs can be positioned to be in fluid communication with an outlet port formed in the housing, and any one of the plurality of reservoirs can be positioned to be in fluid communication with an inlet port formed in the housing;

at least one valve disposed between the plurality of reservoirs and the outlet port, the at least one valve being effective to control the flow of fluid from the plurality of reservoirs to the outlet port, wherein the at least one valve comprises a plunger movable between an open and closed position, and an actuator mechanism effective to move the plunger between the open and closed positions; and a driver mechanism effective to selectively drive fluid from the plurality of reservoirs to the outlet port.

7. The implantable drug pump of claim 6, wherein the actuator mechanism comprises a piezoelectric actuator.

8. The implantable drug pump of claim 1, further comprising a fluid having one or more drugs disposed in at least one of the plurality of reservoirs, and a radiopaque fluid disposed in one of the plurality of reservoirs.

9. The implantable drug pump of claim 1, further comprising a user programmable control mechanism coupled to the drug pump and effective to selectively control movement of the at least one valve between the open and closed positions.

10. An implantable drug pump, comprising:
a housing having a plurality of inlet ports and an outlet port formed therein;

a catheter coupled to the outlet port for delivering fluid to a patient's body;

a plurality of reservoirs disposed within the housing and in fluid communication with at least one of the plurality of inlet ports and with the outlet port;

a plurality of valves, each valve being disposed between one of the plurality of reservoirs and the outlet port, the plurality of valves being effective to control the flow of fluid from the plurality of reservoirs to the outlet port; and a driver mechanism effective to selectively drive fluid from the plurality of reservoirs to the outlet port.

11. The implantable drug pump of claim 10, wherein the driver mechanism is selected from the group consisting of a spring, a propellant gas, and an electromechanical actuator.

12. The implantable drug pump of claim 10, wherein the driver mechanism is adapted to selectively apply a force to at least one of the plurality of reservoirs to cause fluid disposed within the reservoir to be forced through the valve and the outlet port.

13. The implantable drug pump of claim 10, further comprising a controller in communication with the plurality of valves for selectively moving each of the plurality of valves between an open position and a closed position, and an external programmer effective to actuate the controller.

14. The implantable drug pump of claim 10, further comprising a fluid having one or more drugs disposed in at least one of the plurality of reservoirs, and a radiopaque fluid disposed in one of the plurality of reservoirs.

15. The implantable drug pump of claim 10, further comprising a user programmable control mechanism coupled to the drug pump and effective to selectively control movement of each of the plurality of valves between the open and closed positions.

* * * * *